United States Patent [19]

Bruce et al.

[11] Patent Number: 4,695,275
[45] Date of Patent: Sep. 22, 1987

[54] MIDDLE EAR VENTILATION TUBE

[76] Inventors: Donald Bruce, 1723 Peachtree Cir. N., Jacksonville, Fla. 32207; Richard L. Goode, 1583 Arbor, Los Altos, Calif. 94022

[21] Appl. No.: 806,091

[22] Filed: Dec. 6, 1985

Related U.S. Application Data

[63] Continuation of Ser. No. 562,092, Dec. 16, 1983, abandoned.

[51] Int. Cl.$^4$ ............................................. A61M 5/325
[52] U.S. Cl. .................................................... 604/264
[58] Field of Search ................................ 604/264, 284

[56] References Cited

U.S. PATENT DOCUMENTS

| | | |
|---|---|---|
| 2,618,271 | 11/1952 | Wallace . |
| 2,819,719 | 1/1958 | Utley et al. . |
| 3,530,860 | 9/1970 | Majoros . |
| 3,726,284 | 4/1973 | Parker . |
| 3,807,409 | 4/1974 | Paparella et al. . |
| 3,835,863 | 10/1974 | Goldberg ............................ 604/284 |
| 3,871,380 | 3/1975 | Heros ................................... 604/264 |
| 3,982,545 | 9/1976 | Silverstein . |
| 4,309,994 | 1/1982 | Grunwald ............................ 604/284 |

OTHER PUBLICATIONS

Xomed, Myringotomy-Ventilation Tubes (Short Term)-(Long Term), p. 7, and (Short Term), p. 4, copyright 1979.
Richard L. Goode, MD, "T-Tube for Middle Ear Ventilation", May 1973, pp. 402-403, Arch Otolaryngol, vol. 97.

Primary Examiner—John D. Yasko
Attorney, Agent, or Firm—Arthur G. Yeager

[57] ABSTRACT

A myringotomy ventilation tube for insertion into an opening in the tympanic membrane comprising
(a) a tubular body open at both ends;
(b) an outer flange secured to one end of the tubular body and having a rod-like tail member extending outwardly from the flange and adapted to be easily grasped by a medical forceps; and
(c) two inner flexurally resilient arms secured to the other end of the tubular body and extending laterally in opposite directions respectively from the tubular body and adapted to be squeezed together to form a longitudinal extension of the tubular body when inserted into the tympanic membrane opening.

19 Claims, 5 Drawing Figures

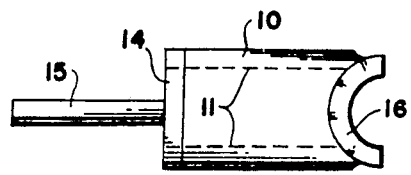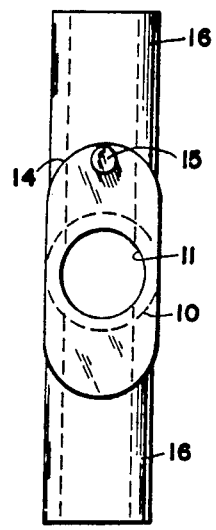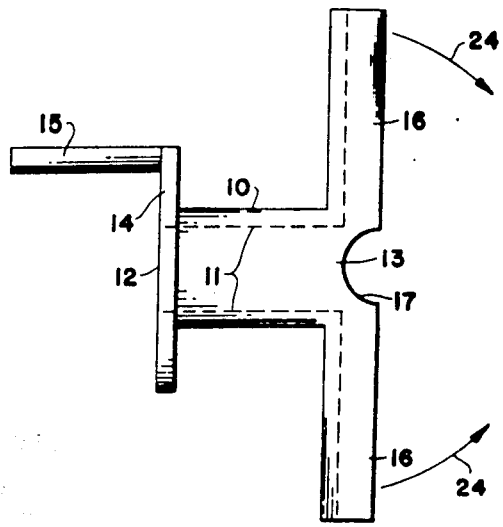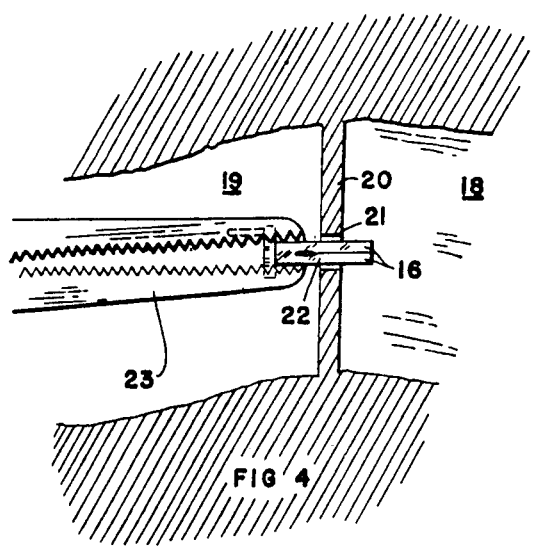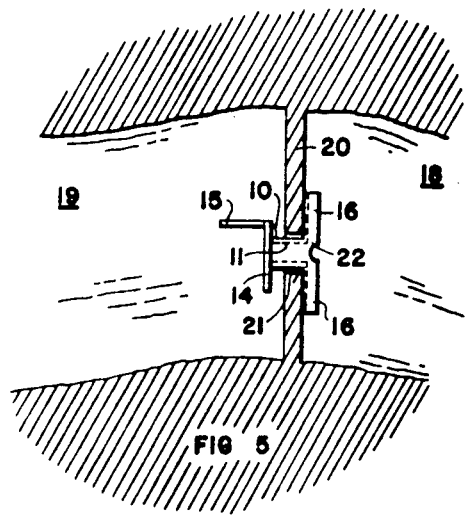

MIDDLE EAR VENTILATION TUBE

This is a continuation of co-pending application Ser. No. 06/562,092, filed on Dec. 16, 1983, now abandoned.

BACKGROUND OF THE INVENTION

There are malfunctions, of the ear, such as eustachian tube insufficiency, and diseases of the ear, such as serous otitis media, which are treated by making an opening or incision in the tympanic membrane and maintaining that opening for a period of time to provide a conduit between the middle ear and the outer ear for drainage or ventilation. The medical term for opening of the tympanic membrane is myringotomy or tympanotomy.

There are known devices to be inserted into the myringotomy opening to keep it open for a period of time. Typical of such devices are those shown in U.S. Pats. Nos. 3,530,860 to Majoros; 3,807,380 to Papparella et al.; 3,835,863 to Goldberg et al.; and 3,871,380 to Heros. These devices suffer from one or more deficiencies. For example, the devices of Majoros and of Goldberg et al. are not capable of use for any long period of time because the body naturally extrudes these devices out of the myringotomy opening, or they may fall into the inner ear. The other two devices are better adapted to remain in place over a long period of time, e.g. a year, but they require a larger myringotomy opening than is desirable. Accordingly there is a need for an improved middle ear ventilation tube.

It is an object of this invention to provide an improved middle ear ventilation or drain tube. It is still another object of this invention to provide a myringotomy ventilation or drain tube that will remain in place for a long period of time with substantially no discomfort to the patient and can be easily removed. Other objects will be apparent in the following more detailed description of this invention.

BRIEF DESCRIPTION OF THE INVENTION

This invention relates to a myringotomy ventilation tube for insertion into an opening in a tympanic membrane to communicate the middle ear with the outer ear, said tube comprising:

(a) a tubular body;

(b) an outer flange secured to one end of said tubular body and having a rod-like tail member extending outwardly from said flange and adapted to be easily grasped by a removal instrument, and (c) two inner flexurally resilient arms secured to the other end of said tubular body, extending laterally in opposite directions from said body, and adapted to be temporarily squeezed together to form a longitudinal extension of said body when being inserted into the opening in the tympanic membrane.

In preferred embodiments of this invention the entire device is made of flexible, resilient silicone rubber that is physiologically acceptable to the body; the outer flange is rectangular or elliptical in shape; and the lateral arms are semitubular in shape.

BRIEF DESCRIPTION OF THE DRAWINGS

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

FIG. 1 is a front elevational view of the device of this invention.

FIG. 2 is a top plan view of the device of this invention.

FIG. 3 is a side elevational view of the device of this invention.

FIG. 4 is a schematic view of the insertion of the device of this invention into a myringotomy opening.

FIG. 5 is a schematic view of the device of this invention in operational position in the tympanic membrane after insertion as shown in FIG. 4.

DETAILED DESCRIPTION OF THE INVENTION

The detailed features of this invention can best be seen in FIGS. 1–3. A tubular body 10 has a central axial bore 11 extending through the device from the outer end 12 to the inner end 13 to provide an open passageway 11 completely through the device. It is not critical that the outer shape of body 10 by cylindrical, although that is the most desirable. The length of body 10 is somewhat larger than the thickness of a tympanic membrane. At outer end 12 there is a flange 14 which is larger in its major dimension than the length of the myringotomy opening in the tympanic membrane so as to prevent flange 14 from passing through that opening. The actual shape of the flange may be circular, square, rectangular, elliptical, or any other convenient shape, although it is preferred to have the shape rectangular or elliptical with the minor axis of the shape being substantially the same as the outside diameter of body 10. This feature of shape of flange 14 provides some facility in inserting the device in the ear by making it easier for the surgeon to see the incision and the tip of the device that is inserted into the incision. Projecting outwardly from flange 14 is tail 15 which serves the purpose of being a handle for easy gripping by medical forceps when the device is to be removed from the ear. The shape of tail 15 is not important, but preferably is rod-like.

At inner end 13 of bore 11 are two lateral arms 16 which extend generally in opposite directions, respectively, from body 10. In cross-section each arm 16 is preferably made in the form of a channel or semitubular so as to provide a certain amount of stiffness to the arm to prevent it from collapsing or folding and thereby being easily extended outwards through the tympanic opening by natural functions of the body. Notch 17 is cut through both sides of arms 16 where they join tubular body 10. Notch 17 makes it easier to squeeze arms 16 against each other by folding in the direction of arrows 24 when the device is inserted through the tympanic opening.

In FIGS. 4 and 5 there is shown the manner in which the device is inserted into the ear and employed as a conduit between the inner ear and the outer ear. Middle ear 18 is separated from outer ear 19 by an impermeable membrane known as the tympanic membrane 20. In a normal ear a eustachian tube connects the middle ear with the nasal cavity so as to permit passage of air (to equalize pressure) or liquid draining out of the middle ear. When that normal situation does not exist the device of this invention is employed to simulate the normal functioning. An incision 21 is made in the tympanic membrane 20. The device of this invention 22 is grasped by alligator forceps 23 so as to fold arms 16 toward each other and to project forwardly of the tip of forceps 23.

Arms 16 are pushed inwardly through incision 21 and forceps 23 are released and withdrawn. Arms 16 will then spring outwardly to their normal lateral position which automatically places the ventilation tube 22 in the desired position as shown in FIG. 5 with arms 16 in the middle ear 18, flange 14 in the outer ear 19, and body 10 passing through the incision 21 in membrane 20. This provides an open passageway 11 from middle ear 18 to outer ear 19. When it is desired to remove the device from the ear, forceps may be inserted into outer ear 19 and grip tail 15 and pulled outwardly causing arms 16 to fold sufficiently to pass through incision 21 and permit removal of the entire device with a minimum of time and discomfort.

The entire device must be made of some flexible, resilient physiologically acceptable material. Silicone rubber is the preferred material for this purpose. In order to have a general understanding of the sizing of a typical device of this invention the following general dimensions are suggested for a tympanic membrane incision of about 2.0–3.5 mm. in length:

Outside diameter of body 10 - 1.5–2.5 mm.
Inside diameter of body 10 - 1.25–2.25 mm.
Length of flange 14 - 3.5–4.5 mm.
Thickness of flange 14 - 0.2–0.4 mm.
Length of each arm 16 - 4–5 mm.
Length of tail 15 - 2–4 mm.
Distance from flange 14 to arm 16 - 2–3 mm.

It is to be understood that these sizes and dimensions may require modification to fit the physical characteristics of the person on whom the device is to be used.

While the invention has been described with respect to certain specific embodiments, it will be appreciated that many modifications and changes may be made by those skilled in the art without departing from the spirit of the invention. It is intended, therefore, by the appended claims to cover all such modifications and changes as fall within the true spirit and scope of the invention.

What is claimed as new and what is desired to secure by Letters Patent of the United States is:

1. A myringotomy ventilation tube for insertion into an opening in a tympanic membrane to allow drainage from a middle ear to an outer ear, said tube comprising:

(a) a hollow tubular body having an outer surface and opposite end portions on opposite side walls of a tympanic membrane and a generally elongated uniform and straight passageway therethrough extending between said end portions and communicating between a middle ear and an outer ear;

(b) an outer flange secured to one of said end portions of said tubular body, said flange having an elongated substantially flat portion for contacting an outer wall of a tympanic membrane and inhibiting said tube from passing through an opening in an tympanic membrane and any contact of the other said end portion with a promotory in a back wall of as middle ear, said flange having a reduced portion substantially conforming to said outer surface of said tubular body for facilitating viewing of an opening in a tympanic membrane during insertion of said tube thereinto;

(c) a projection extending outwardly from said flange adjacent the free edge of said flange and adapted to be readily grasped by a removal instrument, said projection extending substantially parallel to and offset from the longitudinal axis of said passageway; and (d) a pair of spaced inner flexurally resilient elongated separate arms secured to said other end portion of said tubular body spaced from said outer flange and substantially parallel thereto and extending laterally in opposite directions from said body and generally perpendicular to said longitudinal axis, said arms being adapted to be temporarily squeezed together to substantially form a longitudinal extension of said body and having substantially the same diameter thereof and extending parallel to said longitudinal axis when being inserted into an opening in a tympanic membrane and to thereafter return to their opposite directions in perpendicular relationship with respect to said longitudinal axis to contact an inner wall of a tympanic membrane and inhibit inadvertent outward removal of said tube from its placement through an opening in a tympanic membrane.

2. The tube of claim 1 wherein each said lateral arm is defined by a semitubular wall having a surface adjacent the inner wall of a tympanic membrane, each said lateral arm having a curved wall defining an elongated recess extending perpendicular to said longitudinal axis, said recesses of said arms having coincident axes and intersecting said longitudinal axis.

3. The tube of claim 2 wherein said arms and body have juncture portions therebetween, said juncture portions having a pair of spaced notches extending through said semitubular wall aligned along a notch axis which is substantially perpendicular to said longitudinal axis and said coincident axes.

4. The tube of claim 1 in which the longest length of said flange from said longitudinal axis is generally one-half of the length of said legs as measured from said longitudinal axis.

5. The tube of claim 1 wherein said outer flange is substantially elliptical in shape, said reduced portion having an outer surface smoothly merged with a portion of said outer surface of said tubular body and said enlarged portion extending laterally therefrom with said longitudinal axis passing substantially centrally thereof, said projection being attached to said flange offset from the outer wall of said tubular body.

6. The tube of claim 1 wherein said outer flange is substantially rectangular in shape with smoothly curved corners, said reduced portion being smoothly merged with a portion of said outer surface of said tubular body, said longitudinal axis passing substantially centrally of said rectangular shaped flange.

7. The tube of claim 1 wherein said lateral arms are semitubular in shape with the outer wall curved portion thereof being in contact with an inner wall of a tympanic membrane.

8. The tube of claim 7 wherein the juncture of said pair of arms and said body includes a pair of aligned notches in said semitubular wall to facilitate squeezing said two arms together.

9. The tube of claim 8 wherein said outer flange extends in the same direction as said arms with the width of said outer flange and said arms and said tubular body being substantially identical so that said flange and arms are squeezed together in the same direction by an insertion instrument.

10. The tube of claim 1 wherein said outer flange is generally rectangular and the width of said flange and said legs are substantially equal to the diameter of said tubular body.

11. A unitary myringotomy ventilation tube for insertion into an opening in a tympanic membrane to allow drainage from a middle ear to an outer ear, said tube comprising:
  (a) a short hollow cylindrical body having opposite end portions and being of a length longer than a thickness of a tympanic membrane, said body having a generally elongated uniform and straight passageway therethrough extending between said end portions on opposite side walls of a tympanic membrane and communicating between a middle ear and an outer ear;
  (b) an outer flange secured to one of said end portions of said tubular body, said flange having an enlarged substantially flat portion for contacting an outer wall of a tympanic membrane and for inhibiting said tube from passing inwardly through an opening in a tympanic membrane;
  (c) a projecting tail secured to and extending outwardly from said flange adjacent the free edge of said flange and adapted to be readily grasped by a removal instrument, said tail extending substantially parallel to and offset from the longitudinal axis of said passageway; and
  (d) a pair of spaced and separate and enlarged inner flexurally resilient arms secured to the other said end portion of said tubular body spaced from said outer flange and substantially parallel thereto and extending diametrically laterally in opposite directions from said body and generally perpendicular to said longitudinal axis, said arms being temporarily squeezed to substantially form a longitudinal extension of said body and having substantially the same diameter thereof and extending parallel to said longitudinal axis when being inserted into an opening in a tympanic membrane and to resiliently return to their opposite directions in perpendicular relationship with respect to said longitudinal axis to be adjacent to and generally parallel to an inner wall of a tympanic membrane to inhibit inadvertent outward removal of said tube from its placement through an opening in a tympanic membrane.

12. The tube of claim 11 wherein each said lateral arm is defined by a semitubular wall having a surface adjacent the inner wall of a tympanic membrane, each said lateral arm having a curved wall defining an elongated recess extending perpendicular to said longitudinal axis, said recesses of said arms having coincident axes and intersecting said longitudinal axis.

13. The tube of claim 12 wherein said arms and body have juncture portions therebetween, said juncture portions having a pair of spaced notches therethrough aligned along a notch axis which is substantially perpendicular to said longitudinal axis and said coincident axes.

14. The tube of claim 11 wherein said lateral arms are semitubular in shape with the outer wall curved portion thereof being adjacent an inner wall of a tympanic membrane when said tube is located in an opening thereof, said arms and body having juncture portions which include a pair of aligned notches to facilitate squeezing said two arms together.

15. The tube of claim 11 in which the width of said flange and said legs are substantially equal to the diameter of said body, and the longest length of said flange from said longitudinal axis is generally one-half of the length of said legs as measured from said longitudinal axis.

16. The tube of claim 11 wherein said arms are defined by an open channel on the remote side of said arms from said flange, said open channels defining a passageway when said arms are squeezed together.

17. The tube of claim 16 wherein said arms are notched at the juncture with said body to facilitate flexure of said arms when squeezed together.

18. The tube of claim 11 wherein said outer flange is shaped substantially rectangular having a reduced portion conforming substantially the outer diameter of said body, said tail being located offset from the outer wall of said body, said longitudinal axis passing substantially centrally of said rectangular shaped flange.

19. The tube of claim 11 wherein said outer flange is substantially elliptical with the minor axis thereof being substantially equal to the outer diameter of said body and with the major axis thereof intersecting said longitudinal axis substantially perpendicularly.

* * * * *